(12) United States Patent
Sinha et al.

(10) Patent No.: US 11,324,411 B2
(45) Date of Patent: May 10, 2022

(54) METHOD AND SYSTEM FOR DETERMINING CARDIOVASCULAR PARAMETERS

(71) Applicant: Riva Health, Inc., Burlingame, CA (US)

(72) Inventors: Tuhin Sinha, Burlingame, CA (US); Alan Leggitt, Burlingame, CA (US)

(73) Assignee: Riva Health, Inc., Burlingame, CA (US)

(*) Notice: Subject to any disclaimer, the term of this patent is extended or adjusted under 35 U.S.C. 154(b) by 0 days.

(21) Appl. No.: 17/061,114

(22) Filed: Oct. 1, 2020

(65) Prior Publication Data

US 2021/0093210 A1 Apr. 1, 2021

Related U.S. Application Data

(60) Provisional application No. 62/908,758, filed on Oct. 1, 2019.

(51) Int. Cl.
*A61B 5/0295* (2006.01)
*A61B 5/0225* (2006.01)
*A61B 5/00* (2006.01)

(52) U.S. Cl.
CPC ........ *A61B 5/02255* (2013.01); *A61B 5/7203* (2013.01); *A61B 5/7225* (2013.01); *A61B 5/7253* (2013.01)

(58) Field of Classification Search
None
See application file for complete search history.

(56) References Cited

U.S. PATENT DOCUMENTS

| 5,649,543 | A | * | 7/1997 | Hosaka | A61B 5/02255 |
| | | | | | 600/493 |
| 6,337,629 | B1 | * | 1/2002 | Bader | A61B 5/0205 |
| | | | | | 340/575 |
| 6,475,153 | B1 | | 11/2002 | Khair et al. | |
| 6,993,377 | B2 | | 1/2006 | Flick et al. | |
| 7,286,875 | B1 | | 10/2007 | Park et al. | |
| 7,787,946 | B2 | | 8/2010 | Stahmann et al. | |

(Continued)

FOREIGN PATENT DOCUMENTS

| CN | 103826532 A | 5/2014 |
| CN | 104337509 A | 2/2015 |

(Continued)

OTHER PUBLICATIONS

Lee, Han-Wook, et al. "The periodic moving average filter for removing motion artifacts from PPG signals." International Journal of Control, Automation, and Systems 5.6 (2007): 701-706. (Year: 2007).*

(Continued)

*Primary Examiner* — Jacqueline Cheng
*Assistant Examiner* — Jairo H Portillo
(74) *Attorney, Agent, or Firm* — Jeffrey Schox; Randy Mehlenbacher

(57) ABSTRACT

A system and method for determining cardiovascular parameters can include: receiving a plethymogram (PG) dataset, removing noise from the PG dataset, segmenting the PG dataset, extracting a set of fiducials from the PG dataset, and transforming the set of fiducials to determine the cardiovascular parameters.

17 Claims, 10 Drawing Sheets

(56) References Cited

U.S. PATENT DOCUMENTS

| | | |
|---|---|---|
| 8,239,010 B2 | 8/2012 | Banet et al. |
| 8,761,853 B2 | 6/2014 | Thaveeprungsriporn et al. |
| 10,420,515 B2 | 9/2019 | Sinha et al. |
| 2003/0163057 A1 | 8/2003 | Flick et al. |
| 2008/0045818 A1 | 2/2008 | Wood et al. |
| 2009/0326386 A1* | 12/2009 | Sethi .................. A61B 5/7278 600/480 |
| 2010/0168589 A1 | 7/2010 | Banet et al. |
| 2011/0066051 A1 | 3/2011 | Moon et al. |
| 2011/0077531 A1 | 3/2011 | Addison et al. |
| 2011/0224564 A1 | 9/2011 | Moon et al. |
| 2012/0029320 A1 | 2/2012 | Watson et al. |
| 2012/0179011 A1 | 7/2012 | Moon et al. |
| 2012/0190947 A1 | 7/2012 | Chon et al. |
| 2013/0276785 A1 | 10/2013 | Melker et al. |
| 2013/0310656 A1 | 11/2013 | Lim et al. |
| 2013/0345568 A1 | 12/2013 | Mestha et al. |
| 2014/0003454 A1 | 1/2014 | Kaemmerer et al. |
| 2014/0275854 A1 | 9/2014 | Venkatraman et al. |
| 2014/0278220 A1 | 9/2014 | Yuen |
| 2014/0303454 A1 | 10/2014 | Clifton et al. |
| 2015/0037937 A1 | 2/2015 | Park et al. |
| 2015/0080746 A1 | 3/2015 | Bleich et al. |
| 2015/0182132 A1 | 7/2015 | Harris et al. |
| 2015/0324977 A1* | 11/2015 | Magrath .............. A61B 5/0263 382/128 |
| 2015/0379370 A1 | 12/2015 | Clifton et al. |
| 2016/0058375 A1 | 3/2016 | Rothkopf |
| 2016/0256117 A1* | 9/2016 | Baik .................. A61B 5/02055 |
| 2016/0302674 A1 | 10/2016 | Moyer et al. |
| 2016/0360980 A1* | 12/2016 | Sinha .................. A61B 5/4857 |
| 2017/0007137 A1 | 1/2017 | Hong et al. |
| 2017/0071516 A1 | 3/2017 | Bhagat et al. |
| 2017/0079533 A1* | 3/2017 | Robinson .............. A61B 5/6814 |
| 2018/0146865 A1* | 5/2018 | Ortlepp ................ A61B 5/7239 |
| 2019/0059753 A1* | 2/2019 | Chen .................... A61B 5/0456 |
| 2019/0175120 A1* | 6/2019 | Huang .................. A61B 5/044 |

FOREIGN PATENT DOCUMENTS

| | | |
|---|---|---|
| EP | 2992820 A2 | 3/2016 |
| KR | 20160028093 A | 3/2016 |
| WO | 2014022906 A1 | 2/2014 |
| WO | 2015193551 A1 | 12/2015 |

OTHER PUBLICATIONS

Wang, Lu, et al. "Multi-Gaussian fitting for pulse waveform using weighted least squares and multi-criteria decision making method." Computers in biology and medicine 43.11 (2013): 1661-1672. (Year: 2013).*

Perpetuini, David, et al. "Multi-site photoplethysmographic and electrocardiographic system for arterial stiffness and cardiovascular status assessment." Sensors 19.24 (2019): 5570. (Year: 2019).*

Rojano, Juan F., and Claudia V. Isaza. "Singular value decomposition of the time-frequency distribution of PPG signals for motion artifact reduction." Int. J. Signal Process. Syst 4.6 (2016): 475-482. (Year: 2016).*

Elgendi, Mohamed. "Merging digital medicine and economics: Two moving averages unlock biosignals for better health." Diseases 6.1 (2018): 6. (Year: 2018).*

Vadrevu, Simhadri, and M. Sabarimalai Manikandan. "A robust pulse onset and peak detection method for automated PPG signal analysis system." IEEE Transactions on Instrumentation and Measurement 68.3 (2018): 807-817. (Year: 2018).*

"Scholze. Increased arterial vascular tone during the night in patients with essential hypertension. Journal of Human Hypertension (2007) 21, 60-67. published online Oct. 5. [retrieved on Aug. 22, 2016] retrieved from the Internet : http://www.nature.c".

International Search Report and Written Opinion for application No. PCT/US20/053785 dated Jan. 21, 2021.

Sugita, Norihiro , et al., "Techniques for estimating blood pressure variation using video images", 37th Annual International Conference of the IEEE Engineering in Medicine and Biology Society (EMBC) Aug. 29, 2015.

* cited by examiner

METHOD AND SYSTEM FOR DETERMINING CARDIOVASCULAR PARAMETERS

CROSS-REFERENCE TO RELATED APPLICATIONS

This application claims the benefit of U.S. Provisional Application No. 62/908,758, filed 1 Oct. 2019 which is incorporated in its entirety by this reference.

TECHNICAL FIELD

This invention relates generally to the cardiovascular parameters field, and more specifically to a new and useful system and method in the cardiovascular parameters field.

BACKGROUND

The cardiovascular system in humans includes the heart and blood vessels and is central to the distribution of nutrients, hormones, and blood cells throughout the body to maintain homeostasis and combat disease.

Measurement and monitoring of the cardiovascular system has been important in human history. Many biomarkers in the cardiovascular system have been identified for prognostic and diagnostic purposes. Many of these measures are common including heart rate and blood pressure. Others, like heart rate variability, pulse wave velocity and arterial stiffness are evolving in their utility for healthcare professionals and consumers alike.

In many cases, direct measurement of these biomarkers is difficult or prohibitive (e.g., invasive). Inter-arterial pressure, or blood pressure, is an example where direct measurement requires the use of a pressure transducer inserted into one of the major arteries. Due to the risks associated with arterial cannulation, non-invasive assessment of blood pressure is assessed using inflatable cuffs. These instruments usually inflate an air bladder wrapped around the upper arm to temporarily occlude arterial blood flow, and they record the maximum force required to obstruct all flow, and the force at which flow returns (the Korotkoff method). A drawback to this method is that it is incapable of producing real-time beat-to-beat blood pressures.

Thus, there is a need in the cardiovascular detection field to create a new and useful method. This invention provides such new and useful method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 2:
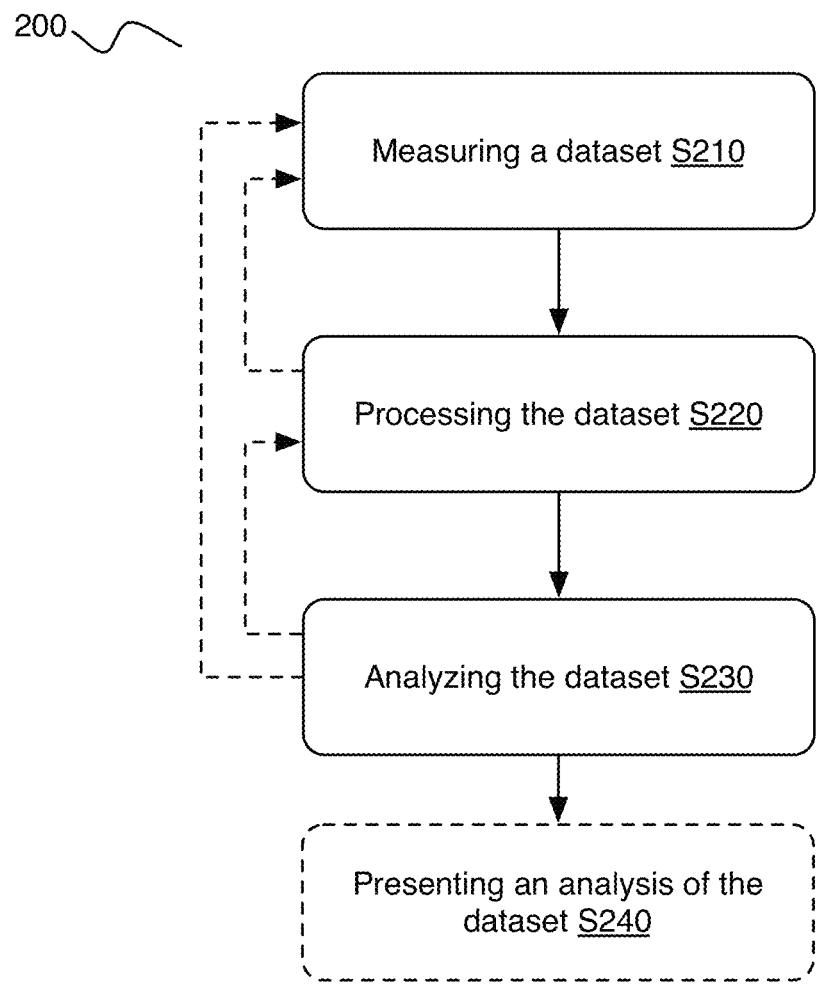
FIG. 2 is an application flow of an embodiment of the method.

As shown in FIG. 2, the method 200 can include measuring an arterial pressure dataset S210, processing the arterial pressure dataset S220, analyzing the arterial pressure dataset S230, and presenting the analysis S240; however, the method can include any suitable steps. Processing the arterial dataset can include: interpolating the dataset S221, filtering the dataset S223, segmenting the dataset S225; denoising the dataset S226; determining a subset of the dataset for analysis S228; and/or any suitable steps.

The method preferably functions to determine one or more cardiovascular parameters (and/or physiological parameters) of an individual. However, the method can additionally or alternatively function to predict the impact of a predetermined activity on the individual's cardiovascular parameters, and/or otherwise function. Examples of cardiovascular parameters include: blood pressure, arterial stiffness, stroke volume, heart rate, blood volume, pulse transit time, phase of constriction, pulse wave velocity, heart rate variability, blood pressure variability, medication interactions (e.g., impact of vasodilators, vasoconstrictors, etc.), cardiovascular drift, cardiac events (e.g., blood clots, strokes, heart attacks, etc.), cardiac output, cardiac index, systemic vascular resistance, oxygen delivery, oxygen consumption, baroreflex sensitivity, stress, sympathetic/parasympathetic tone, and/or any suitable cardiovascular parameters and/or properties. Examples of predetermined activities can include: meditation, exercise regimes (e.g., mild, moderate, strenuous, etc. exercises), medications (e.g., types, dosage, etc.), breathing-exercises, drug intake (e.g., alcohol, caffeine, etc.), and/or any suitable activities.

The method 200 is preferably calibrated to determine an individual's cardiovascular parameters; however, the method can be uncalibrated. In a first variation, the method can be calibrated independently for each individual (e.g., patient, user, etc.). In this variation, calibrating the method can include: measuring a calibrated cardiovascular parameter (e.g., using a blood pressure cuff, sphygmomanometer, radial artery tonometry, arterial catheter, electrocardiogram (ECG), etc.) for an individual and, contemporaneously or substantially simultaneously (e.g., within 15 s, 30 s, 60 s, 2 min, 5 min, 10 minutes, etc.), measuring the cardiovascular parameter of the individual according to the method and/or substeps thereof. In this variation, the method can additionally include: generating an individual manifold based on the fiducials extracted from the individual's' arterial pressure measurements and the cardiovascular parameters, wherein fiducials extracted from subsequent arterial pressure measurements of the individual can be mapped to a cardiovascular state (e.g., including values for one or more cardiovascular parameters) using the individual manifold.

In a second variation, the method can be calibrated for any individual(s) (e.g., whether or not they have previously used the method to determine a cardiovascular parameter). In the second variation, calibrating the method can include: measuring a calibrated cardiovascular parameter (e.g., using a blood pressure cuff, sphygmomanometer, radial artery tonometry, arterial catheter, electrocardiogram (ECG), etc.) for each individual of a control group, contemporaneously or substantially simultaneously (e.g., within 15 s, 30 s, 60 s, 2 min, 5 min, 10 minutes, etc.) measuring the cardiovascular parameter of each individual of the control group according to the method and/or substeps thereof, and determining a universal cardiovascular manifold and/or a general transformation. In the second variation, the universal cardiovascular manifold and/or general transformation can be used to convert a dataset associated with any individual into one or more cardiovascular parameters. For example, the general transformation can convert an individual's fiducials set into a cardiovascular parameter set (e.g., convert a fiducial vector into a cardiovascular parameter vector or cardiovascular state). In a second example, the universal cardiovascular manifold can be used to map a set of fiducial values to the corresponding cardiovascular parameter values. However, the method can be calibrated based on modelling and/or simulations, according to a physical relationship, and/or otherwise be calibrated.

Calibration of the method preferably occurs while an individual and/or individuals of a control group are at rest (e.g., relaxed); however, the calibration process can occur while the individual and/or individuals of a control group are active (e.g., engaged in exercise, engaged in mental exertion, etc.) and/or for any suitable user state. Calibrating the method preferably only needs to be performed once (e.g., for a given user, for a group of users, for all users, etc.); however, the calibration can be performed hourly, daily, weekly, monthly, yearly, and/or with any suitable timing. The method is preferably calibrated to the population as a whole, but can alternatively or additionally be calibrated to a population subset (e.g., segmented based on age, demographic, comorbidity, biomarker combination, and/or other parameter). Calibrating the method preferably produces a transformation (e.g., calibration, equation, look-up table, algorithm, parametrization, etc.) that can be used to determine a cardiovascular parameter from a dataset (and/or fiducial of the dataset). However, the method can be calibrated in any suitable manner.

2. Benefits.

Variations of the technology can confer several benefits and/or advantages.

First, variants of the technology can enable robust, long-term measurements of an individual's cardiovascular parameters. In specific examples, the technology can determine an individual's cardiovascular parameters months after a calibration process without recalibrating the technology.

Second, variants of the technology can enable non-invasive determination of an individual's cardiovascular parameters. In specific examples, the technology can measure an individual's arterial pressure with an individual's device.

Third, variants of the technology can quickly capture and determine an individual's cardiovascular parameters. In specific examples, the technology can leverage computational efficiencies to determine an individual's cardiovascular parameters on a nearly beat-by-beat basis.

Fourth, variants of the technology can confer improvements in a mobile computing device itself that is implementing one or more portions of the method 200, as the mobile computing device can be transformed into a biosignal detector with high specificity in determining relevant cardiovascular parameters. In examples, the technology can enable cardiovascular parameter evaluation using fewer sources of data (e.g., without electrocardiogram data), thus requiring computing systems to process fewer types of data.

Fifth, variants of the technology can leverage imaged-derived signal processing technologies to specifically determine and assess cardiovascular parameters. In specific examples of the technology, the cardiovascular parameters can enable automatic facilitation of therapy provision, including: modulating medication provision, automatically adjusting environmental aspects of the individual to promote health of the individual, providing tailored medical recommendations, facilitating digital communications between patients and care providers, and/or any suitable therapy provision for managing cardiovascular health.

Sixth, the inventors have discovered that, for each individual, the relationship between the individual's fiducials and different cardiovascular parameters are largely constant; changes in the individual's physiological state shifts the fiducials and the cardiovascular parameters in tandem. This allows a static transformation (calibrated to the individual) to be used to determine the individual's cardiovascular parameter value, given the individual's fiducial values, irrespective of the individual's current physiological state. The inventors have further discovered that individuals' fiducial-cardiovascular parameter relationships are all largely similar across a population, such that the fiducial-cardiovascular parameter relationship (e.g., manifold; higher-dimension manifold) for a given individual can be represented as an offset and/or scaled version of a universal manifold (e.g., the individual's fiducial transformation). This allows the individual's manifold (and/or cardiovascular state) to be determined without sampling the full range of the individual's cardiovascular states.

However, variants of the technology can confer any other suitable benefits and/or advantages.

3. System.

Figure 1:
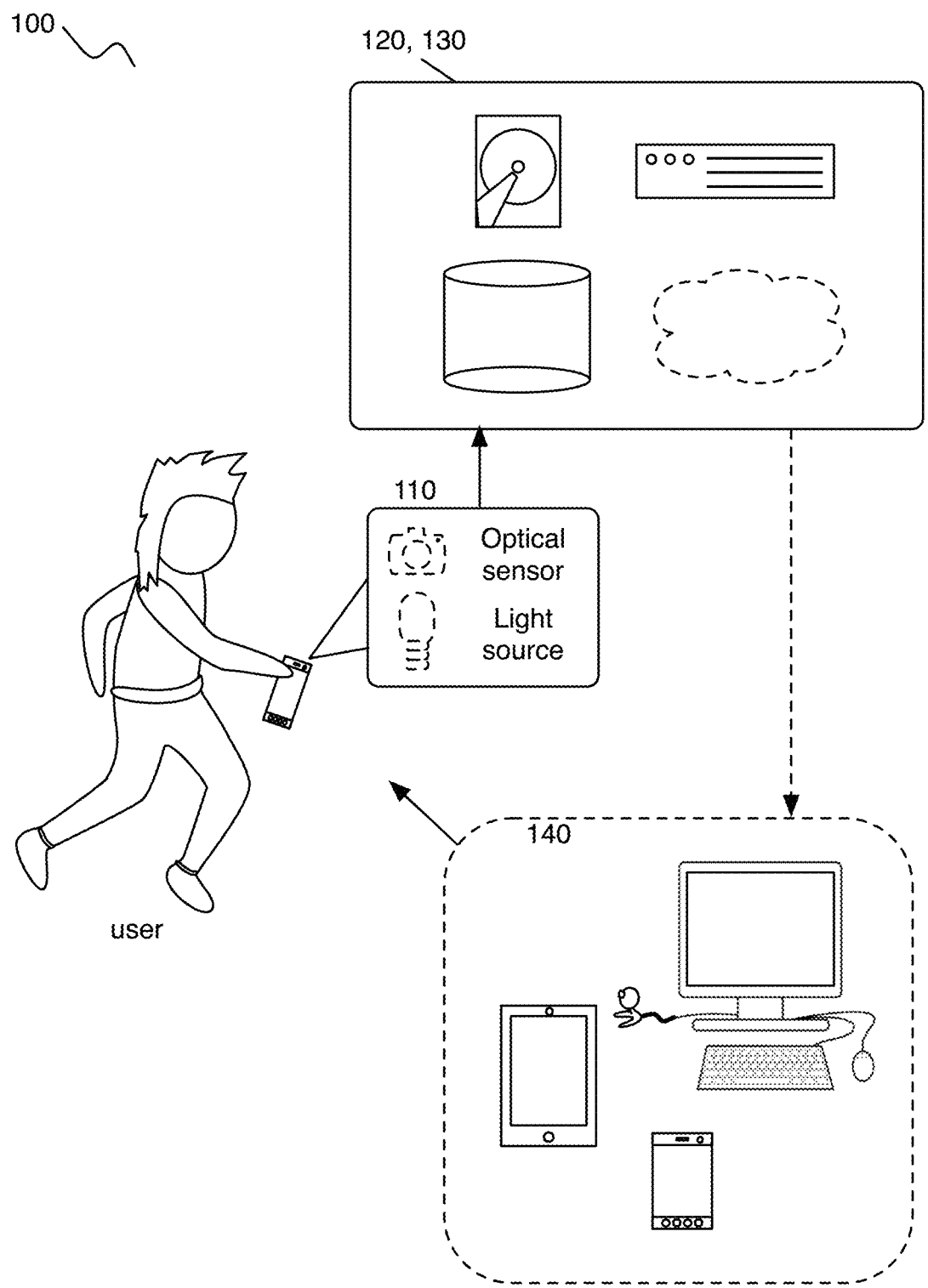
FIG. 1 is a schematic representation of an example of the system.

As shown in FIG. 1, the system 100 can include one or more: data collection modules 110; data processing modules 120; data analysis modules 130; optionally, an interface devices 140; and/or any suitable components. The system 100 can function to measure an arterial pressure dataset (e.g., one or more arterial pressure waveforms) and convert said arterial pressure dataset into one or more cardiovascular parameter (e.g., in real-time, on a pulse-to-pulse basis, etc.). The system preferably enables and/or otherwise performs an embodiment, variation, or example of the method described above, but can additionally and/or alternatively facilitate performance of any suitable method involving determination of cardiovascular parameter variation over time. The system can include one or more modules (e.g., data collection modules, camera module, signal generation module, data processing module, data analysis module, output module, etc.) as disclosed in U.S. patent application Ser. No. 16/538,206 filed 12 Aug. 2019 entitled 'METHOD AND SYSTEM FOR CARDIOVASCULAR DISEASE ASSESSMENT AND MANAGEMENT' and/or U.S. patent application Ser. No. 16/538,361 filed 12 Aug. 2019 entitled 'METHOD AND SYSTEM FOR ACQUIRING DATA FOR ASSESSMENT OF CARDIOVASCULAR DISEASE', each of which is incorporated in its entirety herein by this reference.

The system 100 can include and/or be implemented on one or more of: a user device (e.g., a smart phone, laptop, smart watch, etc.), a remote computing device (e.g., cloud, server, etc.), care-provider device (e.g., dedicated instrument, care-provider smart phone, etc.), and/or at any suitable device. In a specific example, a smart phone of the individual can capture a plurality of images and transmit the plurality of images to a cloud computing server to be processed and/or analyzed.

The data collection module 110 preferably functions to measure one or more datasets (e.g., set of images, arterial pressure dataset, raw dataset, arterial pressure waveform, photoplethysmogram (PPG) dataset, plethysmogram dataset, etc.) relating to an individual's cardiovascular parameters. The data collection module is preferably coupled to the data processing module and data analysis module; however, the data collection module can be in communication with the data processing module, with the data analysis module, and/or configured in any suitable manner.

The arterial pressure dataset is preferably measured at a finger surface of an individual (e.g., detecting arterial pressure waveforms from the radial artery); however, can additionally or alternatively be measured at a wrist surface (e.g., from the ulnar artery), at an upper arm surface (e.g., brachial artery), at a chest surface (e.g., aorta), at a thigh surface (e.g., femoral artery), at an ankle surface of an individual (e.g., tibial artery), and/or at any suitable body region of an individual. The arterial pressure dataset is preferably a series of arterial pressure datapoints (e.g., collected at a predetermined frequency such as 30 Hz, 60 Hz, 120 Hz, 240 Hz, etc. for a predetermined length of time such as 15 s, 30 s, 45 s, 1 min, 2 min, 5 min, etc.); however, the arterial pressure dataset can be single datapoints, and/or any suitable dataset. The arterial pressure dataset is preferably raw data (e.g., primary data); however, the arterial pressure dataset can be any suitable data.

The arterial pressure dataset is preferably measured with the data collection module in contact with the body region of the individual, but can be measured with the data collection module not in contact with the body region of the individual. The data collection module is preferably in contact with the body region of the individual at a substantially constant pressure (e.g., pressure changes by at most 5%, 10%, 20%, etc. during data acquisition), but can be in contact at a variable or changing pressure (e.g., when the contact pressure is measured contemporaneously with the arterial pressure dataset), and/or with any suitable pressure. The data collection module is preferably retained at a substantially fixed orientation (e.g., position changes by less than 100 µm, 1 mm, 1 cm, 5 cm, etc.; orientation changes by less than 0.1°, 1°, 2°, 5°, 10°, etc. with respect to one or more reference axis defined by the body region of the individual and the data collection module; etc.) during data acquisition. However, the data collection module can be moved, reposition, and/or reoriented during data acquisition (such as to improve the quality of the data). In some embodiments, the data collection module can include tracker and/or guide that can function to help the user maintain and/or set a predetermined contact pressure and/or orientation.

The data collection module 110 preferably includes an optical sensor (e.g., a camera); however, the data collection module can include a biosignal sensor (e.g., heart rate monitor, pulsometer, arterial pressure sensor, etc.), a strain gauge, and/or any suitable sensors.

In variants including an optical sensor, the optical sensor preferably functions to measure optical signals (e.g., images, intensity, etc.) from a body region of an individual that are related to the arterial pressure datasets such as PPG data. The optical sensor is preferably associated with a user device; however, the optical sensor can be associated with a guardian device, clinician device, client device, care provider device, and/or any suitable entity. However, the optical device can be a distinct device and/or component thereof, and/or have any suitable form.

The optical sensor can optionally include a light source. The light source can function to provide illumination for the collection of the arterial pressure dataset (e.g., uniform illumination, for low-light conditions, for specific wavelengths of light, specific illumination intensity, etc.). However, the light source can be ambient light (e.g., sunlight, indoor lighting, etc.), and/or any suitable light source.

The data processing module 120 preferably functions to process (e.g., clean such as remove outliers, remove noise, segment, filter, etc.) the arterial pressure datasets into processed datasets; however, the data processing module can process any suitable datasets (e.g., calibration datasets, ECG datasets, PPG datasets, plethysmogram datasets, etc.). The data processing module can perform one or more of the following processes to the dataset: normalizing, removing background, smoothing, cleaning, transforming, fitting, interpolating, extrapolating, segmenting, decomposing (e.g., mode decomposition), denoising, and/or any suitable steps. The data processing module is preferably coupled to the data analysis module; however, the data processing module can be in communication with the data analysis module and/or otherwise suitably arranged.

The data analysis module 130 preferably functions to analyze one or more datasets (e.g., arterial pressure datasets, processed datasets, etc.) to determine one or more cardiovascular parameters of an individual. The data analysis module can perform one or more of the following analyses to the dataset: fitting (e.g., spline, curve, etc.), mathematical operations (e.g., scaling, differentiation, integration, transformation such as Fourier transform, etc.), root-finding, correlation analysis, and/or any suitable analysis. The data analysis module can include equations, look-up tables, conditional statements, learning modules (e.g., neural networks), and/or any suitable analysis tools.

The system can optionally include an interface device 140 (e.g., display) to present cardiovascular parameters, datasets (e.g., analyzed dataset, processed dataset, arterial pressure dataset, etc.), analyses (e.g., fiducials, cardiovascular manifolds, diagnoses, etc.) and/or any suitable data or information to an individual, care-provider, and/or to any suitable entity. However, the data/information can be presented in any suitable manner.

The system 100 can, however, include any other suitable elements configured to receive, process, and/or analyze data in order to promote assessment or management of cardiovascular health of one or more individuals.

4. Method.

The method 200 preferably functions to determine an individual's cardiovascular parameters based on an arterial pressure dataset. The method is preferably performed by a system, such as a system as described above, but can be performed by any system. One or more instances of the method can be performed in series (e.g., sequentially) and/or in parallel (e.g., contemporaneously). Throughout the method, the signals are preferably processed and analyzed in the time domain, but can alternatively be processed and analyzed in the frequency domain, in different domains for different steps, or in any other suitable domain.

Measuring arterial pressure datasets S210 preferably functions to collect a dataset (e.g., arterial pressure dataset, raw dataset, PPG dataset, plethysmogram dataset, etc.) at a body region of an individual. S210 preferably occurs before processing the dataset S220; however, S210 and S220 can occur at the same time and/or with any suitable timing. S210 is preferably performed by a data collection module (e.g., an optical sensor of a data collection module, a strain gauge, etc.); however, any suitable component can be used. In some variants, one or more dataset can be stored (e.g., in a database) and/or retrieved (e.g., from the database). The dataset can be stored as a raw dataset and/or as a processed or analyzed dataset. The dataset is preferably measured at a predetermined frequency or range thereof between 30 and 240 Hz (such as 60 Hz); but can be measured at a frequency less than 30 Hz, greater than 240 Hz, at a variable frequency, and/or with any suitable frequency. The dataset is preferably measured for a predetermined length of time (such as 30 s, 45 s, 1 min, 2 min, 5 min, 10 min, etc.); however, the length of time can be based on the individual (e.g., user's heart rate, the individual activity state, etc.), and/or any suitable length of time.

S210 can optionally include receiving, acquiring, and/or generating a supplemental dataset. Examples of supplemental dataset can include: characteristics of the individual (e.g., height, weight, age, gender, race, ethnicity, etc.), medication history of the individual (and/or the individual's family), activity level (e.g., recent activity, historical activity, etc.) of the individual, medical concerns, healthcare profession data (e.g., data from a healthcare professional of the individual), and/or any suitable supplemental dataset.

In a specific example, S210 can include positioning the data collection module (e.g., at a body region of an individual), illuminating the body region of the individual (e.g., using the light source, using ambient light, etc.), measuring a light scattering parameter (e.g., reflection, absorption, etc.), and recording a series of light scattering parameters to generate an arterial pressure dataset. The light scattering parameter is preferably measured a data collection frequency greater than or equal to about 60 Hz, however, any suitable data collection frequency can be used. However, generating arterial pressure datasets can be performed in any suitable manner.

In a second specific example, S210 can include positioning the data collection module (e.g., at a body region of an individual), illuminating the body region of the individual (e.g., using the light source, using ambient light, etc.), measuring a plurality of images of the body region, and generating a photoplethymogram (PPG) dataset from the plurality of images. The PPG dataset can be generated from the plurality of images by extracting one or more features from the images, determining an optic flow depth map between of images, recording a change in a pixel property across images, and/or can be otherwise generated from the plurality of images.

In a third specific example, S210 can include one or more steps of data acquisition as disclosed in U.S. patent application Ser. No. 16/538,361, which is incorporated herein in its entirety.

However, S210 can include any suitable steps and/or be performed in any manner.

Processing a dataset S220 preferably functions to transform a dataset (e.g., raw dataset, arterial pressure dataset, etc.) into a processed dataset (e.g., improve signal to noise, segment the dataset, remove outliers from the dataset, etc.). In a specific example, the raw datasets can include large, nonstationary backgrounds (e.g., from variations in contact pressure between the body region and the data collection module, variations in orientation between the body region and the data collection module, random noise, etc. over the duration of the measurement). In this specific example, processing the datasets can remove the nonstationary backgrounds. However, processing arterial pressure datasets can generate any suitable datasets and/or perform any suitable function.

Processing a dataset preferably occurs after measuring the dataset; however, processing a dataset can occur after any subset of the dataset is measured. S220 preferably occurs before analyzing the dataset S230; however, S220 can occur at the same time as S230, after S230 (e.g., processing data if during data analysis an error occurs), and/or with any suitable timing. S220 is preferably performed by a data processing module; however, S220 can be performed by any suitable component. The dataset is preferably processed in a cloud computing system, but can be processed by a user device, a local computing system and/or in any suitable location.

Figure 3:
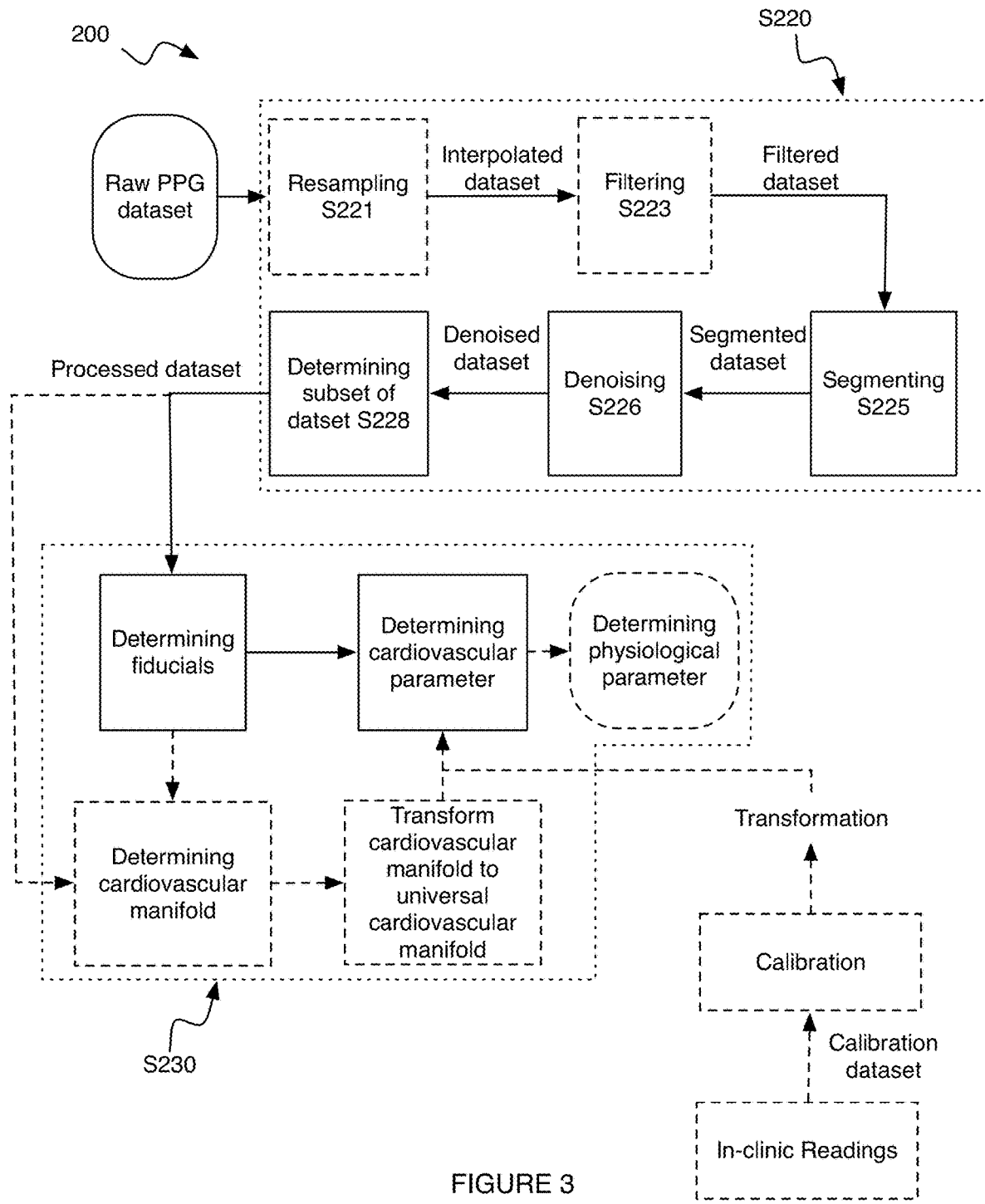
FIG. 3 is an application flow of an embodiment of the method.
Figure 4:
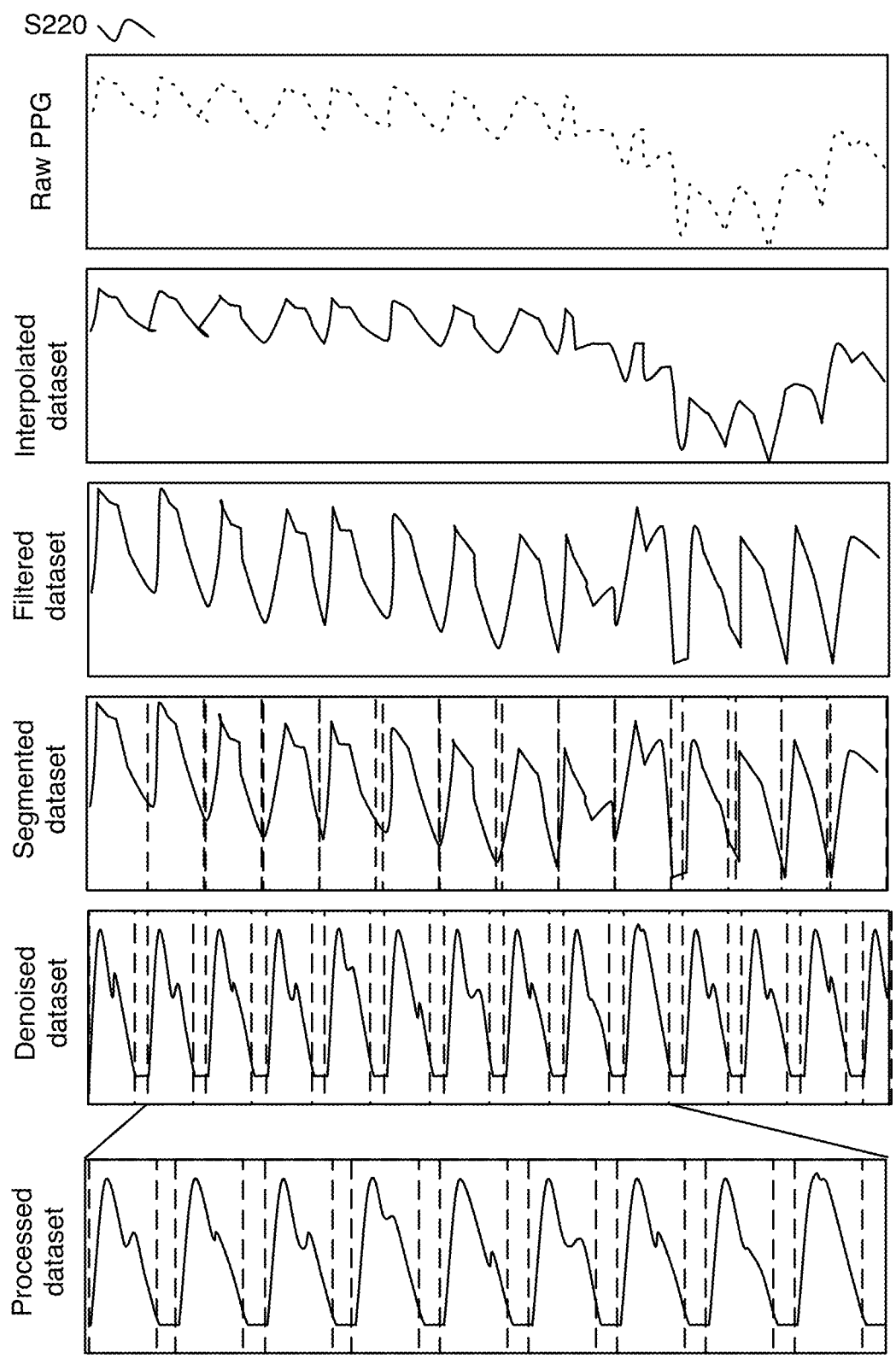
FIG. 4 is a schematic representation of an example of processing the dataset.

As shown for example in FIGS. 3 and 4, S220 can include: resampling the dataset S221; filtering the dataset S223; segmenting the data S225; denoising the dataset S226; determining a subset of data to analyze S228; and/or any suitable steps.

S221 preferably functions to insert new and/or remove extraneous datapoints (e.g., between already existing datapoints) into a dataset (e.g., raw dataset, arterial pressure dataset, PPG dataset, plethysmogram dataset, etc.) so that the dataset (e.g., interpolated dataset, interpolated raw dataset, etc.) contains datapoints spaced with a predetermined frequency/period. S221 preferably occurs before S226; however, S221 can occur at the same time as S226 and/or after S226. The predetermined frequency is preferably a multiple of 60 Hz (e.g., 120 Hz, 240 Hz, etc.); however, the predetermined frequency can be chosen based on the number of datapoints in the dataset (e.g., total number of datapoints), can vary (e.g., be lower in data sparse regions such as to sample the dataset with fewer datapoints; be higher in data rich regions such as to sample the dataset with more datapoints; etc.), and/or any suitable frequency can be used. New datapoints are preferably determined by interpolating between the nearest neighboring datapoints, but can additionally or alternatively be generated by interpolating between any suitable neighboring datapoints, using machine learning, by fitting the data to a curve, using simulations, and/or otherwise generating additional data. The interpolation is preferably linear; however, nonlinear interpolation and/or any suitable interpolation can be used. Datapoints are preferably removed such that the time spacing between data points is a constant (e.g., based on the predetermined frequency), but can additionally or alternatively be removed to remove bad data (e.g., outliers, artifacts, etc.), and/or otherwise be removed.

S223 preferably functions to improve the signal-to-noise ratio (SNR) of the dataset (e.g., arterial pressure dataset, raw dataset, interpolated dataset, interpolated raw dataset, etc.) by applying one or more filters to generate a filtered dataset. S223 preferably occurs before S225; however, S223 can occur at the same time as and/or after S225. The filter can be a short-pass filter (e.g., with a cut-off frequency of <0.1 Hz, 0.1, 0.5, 1, 10, 20, 30, 60, 100, 200, 500, 1000, >1000 Hz, etc.), long-pass filter (e.g., with a cut-off frequency of <0.1 Hz, 0.1, 0.5, 1, 10, 20, 30, 60, 100, 200, 500, 1000, >1000 Hz, etc.), bandpass filter (e.g., by combining a long-pass and short-pass filter), notch or band-stop filter, and/or any suitable filter. In a specific example, the filter can be a long-pass filter that can remove signals less than 0.5 Hz from the dataset; however, any suitable cut-off filter can be used. The filter can be applied to the dataset in the time and/or frequency domain. The whole dataset is preferably filtered at the same time; however, one or more subsets of the dataset can be filtered at a time and/or filtering the dataset can be performed in any suitable manner. In an illustrative example, each segment of a segmented dataset (e.g., segmented dataset such as generated in Step S225, S226, or S228) can be filtered (e.g., using the same or different filters). In a second illustrative example, a raw and/or interpolated dataset can be filtered. However, any suitable dataset or sets can be filtered.

S225 preferably functions to identify each distinct physiological cycle (e.g., heartbeat, cardiac cycle, respiratory cycle, digestive cycle, etc.) and its corresponding arterial pressure waveform within a dataset (e.g., arterial pressure dataset, interpolated dataset, filtered dataset, etc.) and to generate a segmented dataset. The segmented dataset is preferably segmented into individual heartbeats; however, the segmented dataset can be segmented into sets of heartbeats (e.g., heartbeats wherein the arterial pressure waveform shows little variance, heartbeats in close temporal proximity, etc.), into individual arterial pressure waveform components (e.g., direct transmission; reflected arterial pressure signals such as from the iliac artery, renal artery, etc.; etc.), and/or segmented into any suitable form. S225 preferably occurs before S226; however, S225 can occur at the same time as and/or after S226. Each segment is preferably the same size (e.g., same time window, same frequency window, etc.); however, the segments can have any suitable size. Segments are preferably distinct (e.g., non-overlapping); however, segments can overlap and/or have any suitable relationship to other segments.

The segmented dataset is preferably segmented using a slow and fast-moving average (e.g., moving average crossover); however, the segmented dataset can be segmented using derivative methods, integral methods, threshold methods, variational methods, machine learning (e.g., using a trained neural network), pattern matching (e.g., segmented whenever a dip is detected), and/or be segmented in any suitable manner. In a specific example, beat segmentation using a slow and fast moving average is applied to each point in the interpolated dataset.

S226 preferably functions to denoise a dataset (e.g., raw dataset, interpolated dataset, filtered dataset, segmented dataset, etc.) to improve the SNR of the dataset and to generate a denoised dataset (e.g., denoised segmented dataset). S226 preferably occurs before S228; however, S226 can occur at the same time as S228 and/or after S228. S226 is preferably performed after S225, but can be performed before and/or at the same time as S225.

In specific variants, S226 can include decomposing the dataset into intrinsic modes. In these variants, decomposing the data into intrinsic modes can speed up the processing, reduce the processing resources, and/or perform any suitable function. Each segment of the segmented dataset is preferably independently decomposed into intrinsic modes. However, a dataset (e.g., segmented dataset, filtered dataset, raw dataset, etc.) can be decomposed into intrinsic modes as a whole, a plurality of segments can be decomposed together, and/or the dataset can be decomposed into intrinsic modes in any manner. The intrinsic modes can correspond to discrete modes and/or continuous modes (e.g., such as frequencies of a continuous transform).

In a specific example of this specific variant, each intrinsic modes can encode differing amounts of signal data (e.g., data that is related to the cardiovascular parameter) and noise data. The specific intrinsic modes that encode signal data (e.g., primarily encode signal data, such as: $1^{st}$, $2^{nd}$, $3^{rd}$, $4^{th}$, $5^{th}$, $6^{th}$, $7^{th}$, $8^{th}$, $9^{th}$, $10^{th}$, $15^{th}$, $20^{th}$, etc.) can be included in denoised data and modes that encode noise data (e.g., primarily encode noise data such as any mode after the $1^{st}$, $2^{nd}$, $3^{rd}$, $4^{th}$, $5^{th}$, $6^{th}$, $7^{th}$, $8^{th}$, $9^{th}$, $10^{th}$, $15^{th}$, $20^{th}$, etc. modes) can be excluded from the denoised data. Including modes in the denoised dataset preferably includes adding each of the modes to include to the dataset, but can additionally or alternatively include calculating an average of the modes to be included, and/or otherwise combining the intrinsic modes. The intrinsic modes that primarily encode the data can be the first mode, first two modes, first three modes, first four modes, first five modes, first ten modes, second to fourth mode, second to sixth modes, first half of the modes, last half of the modes, first third of the modes, second third of the modes, last third of the modes, first quarter of the modes, first tenth of the modes, subsets thereof, and/or any suitable modes. However, the denoised data can be generated in any suitable manner.

The intrinsic modes are preferably determined using enhanced empirical mode decomposition (EEMD); however, the intrinsic modes can be determined using empirical mode decomposition (EMD), Hilbert transformation, machine learning, principal component analysis (PCA), decomposition of the dataset into any suitable basis set (e.g., an orthogonal basis set, orthonormal basis set, etc.), fitting the dataset (e.g., polynomial fit, noise model, to an equation, etc.), and/or in any suitable manner. The intrinsic modes can be determined in the frequency and/or time domain. Intrinsic modes are preferably determined for each segment (e.g., arterial pressure data associated with a given heartbeat) separately; however, intrinsic mode analysis can be performed on the dataset in its entirety, and/or any suitable subset of the dataset can be used.

In a specific example, the EEMD analysis of the dataset can decompose the dataset into approximately 20 intrinsic modes (e.g., ±5 modes, ±10 modes, ±20 modes, etc.). In this example, intrinsic modes 1-6 can be chosen to generate the denoised dataset; however, any suitable modes can be used. The denoised dataset can be generated by summing intrinsic modes 1-6 (e.g., excluding the remaining intrinsic modes). However, denoising the dataset can be performed in any suitable manner.

S228 preferably functions to determine one or more subsets of the dataset (e.g., denoised dataset, segmented dataset, filtered dataset, interpolated dataset, raw dataset, etc.) to include in a processed dataset. The subset of the dataset is preferably determined based on the SNR within the subset; however, completeness of data, intermediate precision, and/or based on any suitable data quality metric.

The processed dataset preferably includes any suitable number and/or range of segments between 1-1000 such as 30 segments; however, the entire dataset (e.g., denoised dataset, segmented dataset, filtered dataset, interpolated dataset, raw dataset, etc.) can be included in the processed dataset, and/or any suitable number of segments can be included. The segments included in the processed dataset are preferably sequential (e.g., do not skip any heartbeats);

however, the processed dataset can skip any number of suitable segments, and/or include any suitable data. The number of segments contained in the dataset can depend on the calibration method, the cardiovascular parameters to determine, a target and/or threshold time span, and/or be otherwise determined. In an illustrative example, when the cardiovascular parameter to determine includes blood pressure, the processed dataset preferably includes approximately 10 contiguous segments (e.g., can discretely detect approximately 10 cardiac cycles such as heartbeats in sequence). However, any number of contiguous segments can be used.

In a specific embodiment of S228, the subset(s) of the dataset can be determined based on a moving time window SNR. The time window can be any suitable time window or range thereof between 0-120 sec, such as 15 sec; however, any time window can be used. The time window preferably begins at one segment of the dataset (e.g., one heartbeat), but can additionally or alternatively encompass multiple heartbeats or portion thereof. After comparing the SNR within the time window to an SNR threshold (e.g., 1, 2, 10, 20, etc.), when the SNR within the time window is greater than or equal to the SNR threshold, the segment(s) within the time window can be included within the processed dataset and a subsequent time window can be examined (e.g., the time window to be examined can shift by one or more segments and the analysis repeated). However, when the SNR within the time window is less than the SNR threshold, the segment(s) can be rejected. When no suitable subset of the dataset can be determined (e.g., too many segment(s) are rejected), a new dataset can be measured (e.g., by repeating S210), the dataset can be reprocessed (e.g., by repeating one or more steps of S220 such as steps S221-S226), and/or any suitable process can occur. However, the segment(s) included in the processed dataset can be determined in any suitable manner.

Analyzing the dataset S230 preferably functions to determine one or more cardiovascular parameters of the individual from the dataset (e.g., processed dataset, denoised dataset, segmented dataset, filtered dataset, interpolated dataset, raw dataset, etc.). S230 can additionally or alternatively function to determine fiducials (and/or any other suitable parameters) associated with the cardiovascular parameters of the individual. The dataset can be analyzed on a per segment basis (e.g., cardiovascular parameters determined for each segment), for the dataset as a whole, for an averaged dataset (e.g., averaging the segments associated with the subset of the dataset identified in S228 with other segments on a timestep by timestep basis), and/or otherwise be analyzed. S230 is preferably performed by a data analysis module; however, any suitable component can be used. S230 is preferably performed at a cloud computing system, but can be performed at a user device, a local computing system, and/or by any computing system. S230 is preferably performed independently for each segment of the dataset; however, S230 can be performed for the entire dataset, the analysis of one segment can depend on the results of other segments, and/or any suitable subset of the dataset can be analyzed. The analysis is preferably transmitted to the user device and/or the interface device, but can additionally or alternatively be transmitted to a care provider, guardian, database, and/or any suitable endpoint.

The cardiovascular parameter(s) can be determined based on the dataset, fiducials, and/or cardiovascular manifold using regression modeling (e.g., linear regression, nonlinear regression, etc.), learning (e.g., a trained neural network, a machine-learning algorithm, etc.), an equation, a look-up table, conditional statements, a transformation (e.g., a linear transformation, a non-linear transformation, etc.), and/or determined in any suitable manner.

The transformation (e.g., correlation) between the fiducials and/or the cardiovascular manifold and the cardiovascular parameters is preferably determined based on a calibration dataset (e.g., a calibration dataset such as from a blood pressure cuff, ECG measurements, etc. generated at approximately the same time as the analysis dataset; a second arterial pressure dataset such as at a different body region of the individual, of a different individual, of the individual in a different activity state, etc.; a calibration dataset including an analysis dataset for each individual of a control group with a corresponding measured cardiovascular parameter; etc.); however, the transformation can be determined from a model (e.g., a model of the individual's cardiovascular system, a global model such as one that can apply for any user, etc.), and/or determined in any suitable manner.

S230 can include: determining fiducials S232; determining cardiovascular parameters S236; and storing the cardiovascular parameters S239. However, S230 can include any suitable processes.

S232 preferably functions to determine fiducials for the dataset (e.g., processed dataset, denoised dataset, segmented dataset, filtered dataset, interpolated dataset, raw dataset, etc.). S232 preferably occurs before S236; however, S232 can occur at the same time as and/or after S236. The set of fiducials can depend on the cardiovascular parameters, characteristics of the individual, the supplemental dataset, and/or any suitable information. In some variants, different fiducials can be used for different cardiovascular parameters; however, two or more cardiovascular parameters can be determined from the same set of fiducials.

Figure 8:
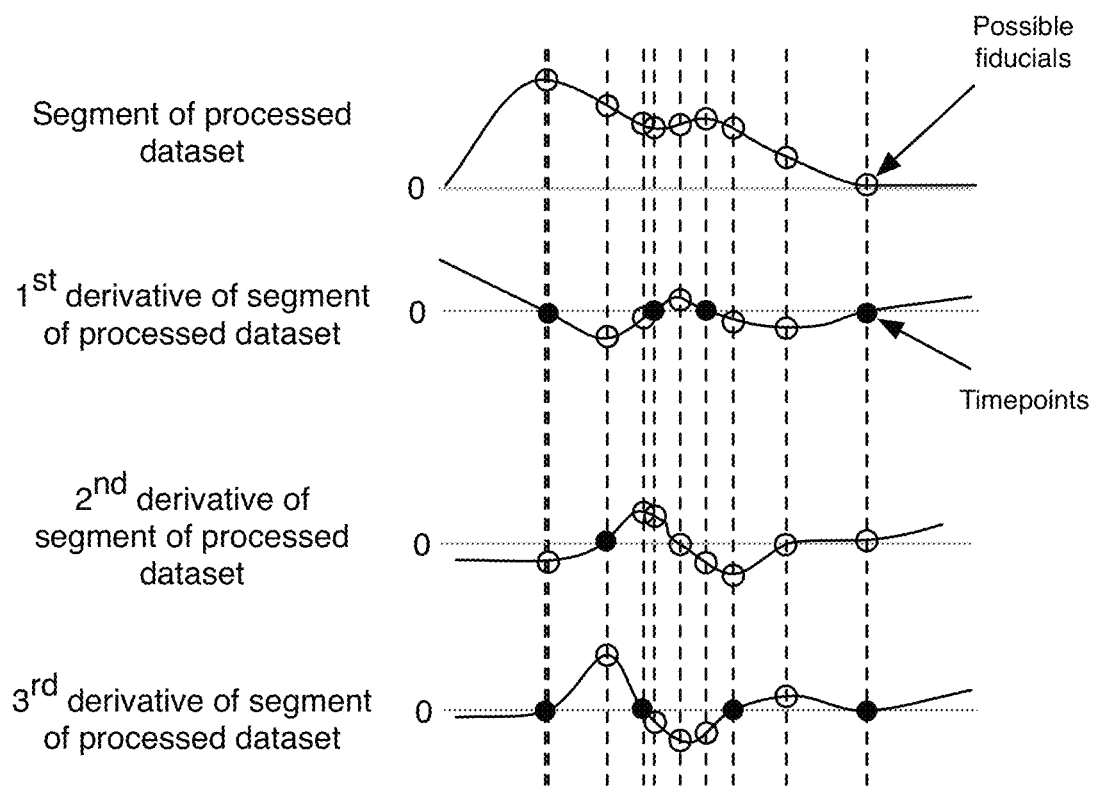
FIG. 8 is a schematic representation of an example of possible fiducials (e.g., any or all of the circled points) associated with a processed dataset, a first derivative of the processed dataset, a second derivative of the processed dataset, and a third derivative of the processed dataset.

In a first variant of S232, determining the fiducials can include optionally: spline fitting the processed dataset, computing derivatives (e.g., first, second, third, higher order, etc.) of the spline fit dataset, and determining roots (e.g., zeroes) in one or more of the derivatives. The fiducial(s) can be one or more of the roots of the derivatives, the values of the dataset and/or other derivatives evaluated at the roots of a derivative, and/or otherwise be determined. In a first specific example, the fiducials can include two roots of the second derivative and one root of the third derivative; however, the fiducials can be the amplitude of the dataset (e.g., evaluated at one of the roots), the amplitude of any suitable derivative of the dataset (e.g., evaluated at one of the roots), and/or any suitable roots and/or values of the dataset. In a second specific example, the fiducials can correspond to the values of the processed dataset and the first and second derivatives of the processed dataset evaluated at time points corresponding to the first four zeros (e.g., relative to the start of a segment, relative to a peak of the processed dataset, relative to a prior cardiac cycle, etc.) of the first and second derivatives of the process dataset. In a third specific example, as shown in FIG. 8 the fiducials can correspond to the set and/or any subset thereof of the: amplitude of the processed dataset (and/or one or more segment thereof), amplitude of the first derivative of the processed dataset (and/or one or more segment thereof), amplitude of the second derivative of the processed dataset (and/or one or more segment thereof), and amplitude of the third derivative of the processed dataset (and/or one or more segment thereof) evaluated at a root of the first derivative, second derivative, and/or third derivative. In FIG. 8, the zeros of the respective derivatives are identified as the timepoints of interest (illustrated in FIG. 8 filled-in circles), wherein the values of each derivative at each of the time-points of interest are fiducial candidates. In a fourth specific example, the fiducials can be selected from and/or include any of the following values:

p(g), p"(g), p'"(g), p(h), p'(h), p'"(h), p(k), p'(k), p"(k)

Where p(a) is the processed dataset (and/or a segment thereof) at time a, p' is the first derivative of p with respect to time, p" is the second derivative of p with respect to time, p'" is the third derivative of p with respect to time, g corresponds to a set of times such that p'(g)=0, h corresponds to one or more times such that, p"(h)=0, and k corresponds to one or more time such that p'"(k)=0.

In a second variant of S232, determining the fiducials can include decomposing the processed dataset (e.g., for each segment in the analysis dataset) into any suitable basis function(s). In a specific example, decomposing the processed dataset can include performing a discrete Fourier transform, fast Fourier transform, discrete cosine transform, Hankel transform, polynomial decomposition, Rayleigh, wavelet, and/or any suitable decomposition and/or transformation on the processed dataset. The fiducials can be one or more of the decomposition weights, phases, and/or any suitable output(s) of the decomposition. However, the fiducials can be determined from the dataset in any suitable manner.

In a third variant of S232, determining the fiducials can include fitting the processed dataset to a predetermined functional form. The functional form can include gaussians, Lorentzians, exponentials, super-gaussians, Levy distributions, hyperbolic secants, polynomials, convolutions, linear and/or nonlinear combinations of functions, and/or any suitable function(s). The fitting can be constrained or unconstrained. In a specific example, a linear combination of 5 constrained gaussians (e.g., based on user's cardiovascular state and/or phase) can be used to fit each segment of the data. However, any suitable fit can be performed. The fiducials are preferably one or more of the fit parameters (e.g., full width at half max (FWHM), center position, amplitude, frequency, etc.); however, the fiducials can include statistical order information (e.g., mean, variance, skew, etc.) and/or any suitable information.

Determining the cardiovascular parameters S236 preferably functions to determine the cardiovascular state (e.g., set of cardiovascular parameter values) for the user. The cardiovascular parameters can be determined based on the fiducials, based on the cardiovascular manifold, and/or otherwise be determined. S236 preferably determines cardiovascular parameters relating to each segment of the dataset (e.g., each heartbeat); however, S236 can determine a single cardiovascular parameter value for the entire dataset (e.g., a mean, variance, range, etc.), a single cardiovascular parameter, and/or any suitable information. S236 preferably occurs before S239; however, S236 can occur simultaneously with and/or after S239.

Figure 7A:
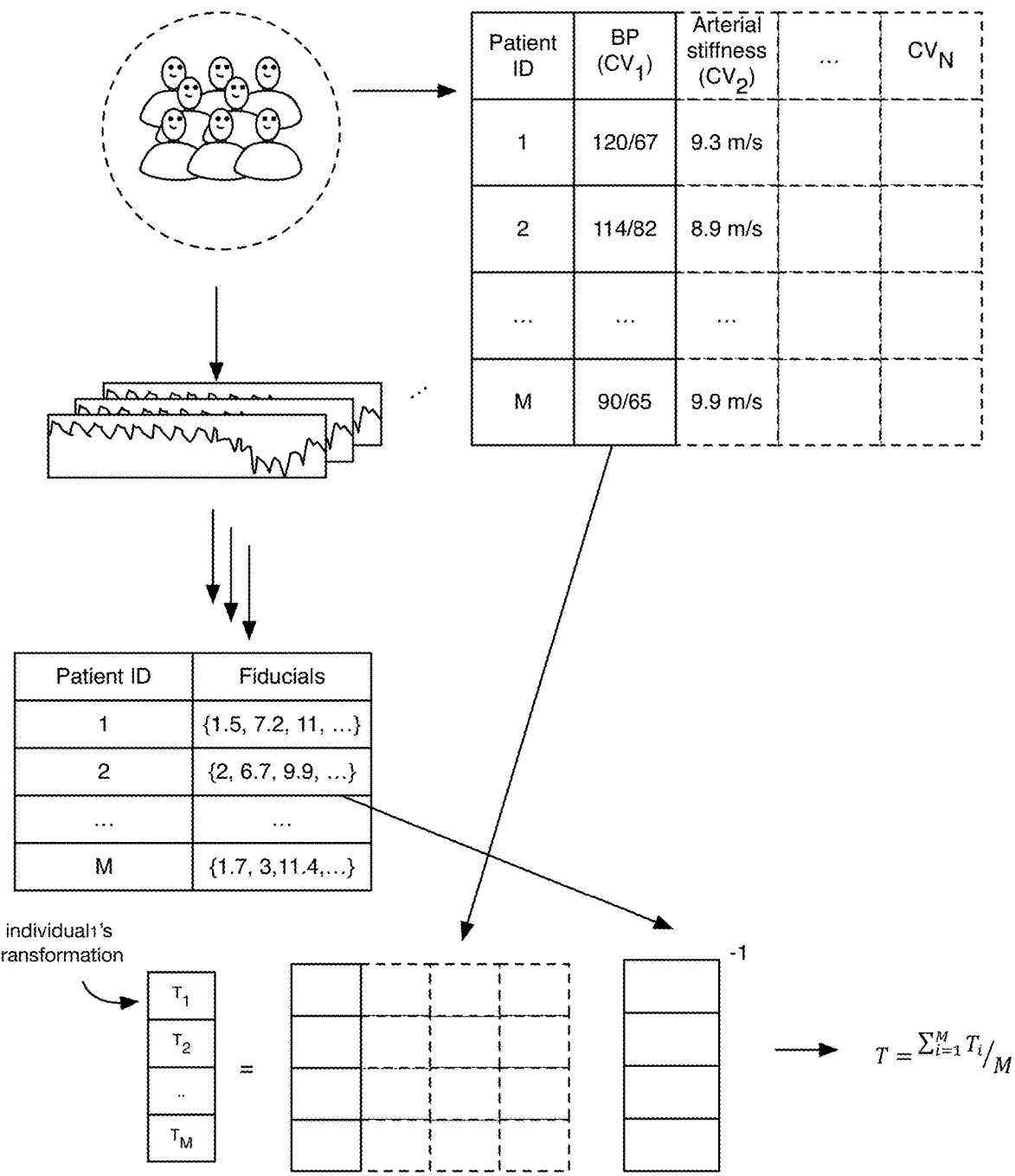
FIG. 7A is a schematic representation of an example of determining a transformation by measuring a set of fiducials for each member of a control group, contemporaneously measuring one or more cardiovascular parameter of the control group (e.g., $CV_1$, $CV_2$, . . . , $CV_N$, such as blood pressure, arterial stiffness, etc.), and determining a transformation (T) that relates the fiducials to the cardiovascular parameter(s).
Figure 7B:
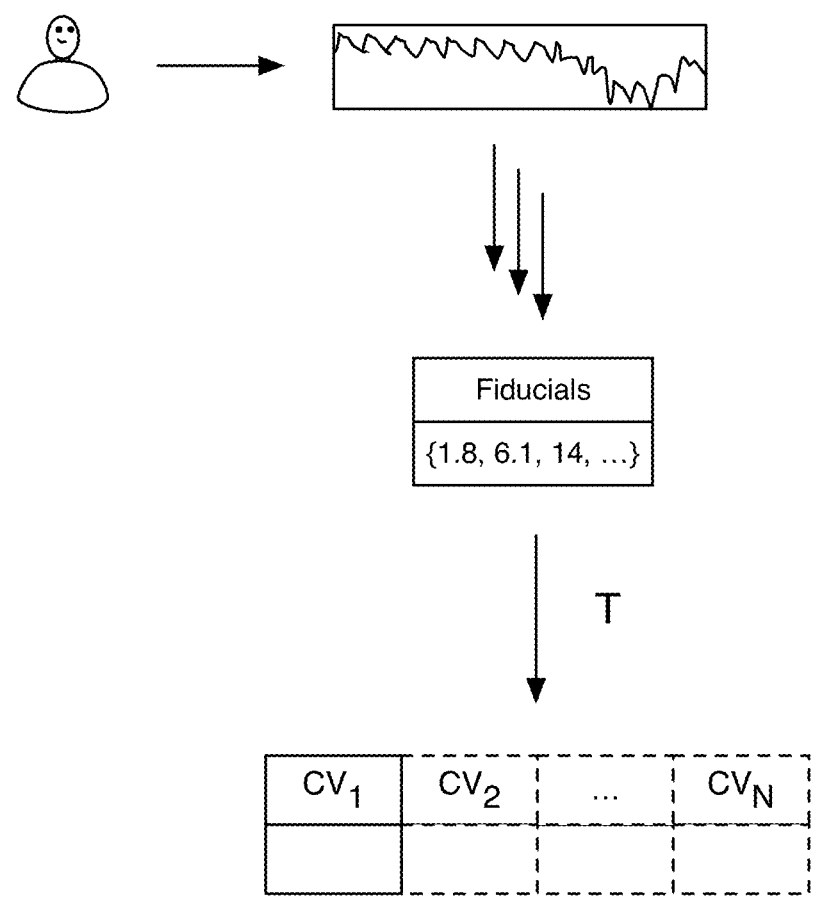
FIG. 7B is a schematic representation of an example of determining a cardiovascular state of an individual based on the transformation of FIG. 7A and individual's fiducials.

In a first variant of S236, as shown for example in FIG. 7B, the cardiovascular parameters can be determined by applying a fiducial transformation to the set of fiducials (e.g., determined in S232). The fiducial transformation can be determined from a calibration dataset (e.g., as shown in FIG. 7A, wherein a set of fiducial transforms for different individuals are determined by multiplying the cardiovascular parameters by the inverse matrix of the respective fiducials), based on a model (e.g., a model of the individual, a model of human anatomy, a physical model, etc.), generated using machine learning (e.g., a neural network), generated from a manifold (e.g., relating fiducial value sets with cardiovascular parameter value sets), based on a fit (e.g., least squares fit, nonlinear least squares fit, etc.), and/or be otherwise determined. The fiducial transformation can be a universal transformation, be specific to a given cardiovascular parameter or combination thereof, be specific to the individual's parameters (e.g., age, demographic, comorbidities, biomarkers, medications, estimated or measured physiological state, etc.), be specific to the individual, be specific to the measurement context (e.g., time of day, ambient temperature, etc.), or be otherwise generic or specific. The fiducial transformation can be the average, median, most accurate (e.g., lowest residuals, lowest error, etc.), based on a subset of the control group (e.g., a subset of the control group with one or more characteristics similar to or matching the individual's characteristics), selected based on voting, selected by a neural network, randomly selected, and/or otherwise determined from the calibration dataset.

The fiducial transformation (e.g., linear regression coefficients) can be a linear or nonlinear transformation. Each cardiovascular parameter can be associated with a different fiducial transformation and/or one or more cardiovascular parameters can be associated with the same fiducial transformation (e.g., two or more cardiovascular parameters can be correlated or covariate). In a specific example of the first variant, the cardiovascular parameters can be determined according to:

$$AT=B$$

where A corresponds to the set of fiducials, T corresponds to the fiducial transformation, and B corresponds to the cardiovascular parameter(s).

In a specific example, the method includes: determining the fiducial transformation for an individual, and determining the cardiovascular parameter value(s) for the individual based on a subsequent cardiovascular measurement and the fiducial transformation. The fiducial transformation is preferably determined from a set of calibration data sampled from the individual, which can include: fiducials extracted from calibration cardiovascular measurements (e.g., PPG data, plethysmogram data) (A), and calibration cardiovascular parameter measurements (e.g., blood pressure, $O_2$ levels, etc.; measurements of the cardiovascular parameter to be determined) (B). The fiducial transformation (T) for the individual is determined from AT=B. T is subsequently used to determine the cardiovascular parameter values for fiducials extracted from subsequently-sampled cardiovascular measurements.

Figure 6A:
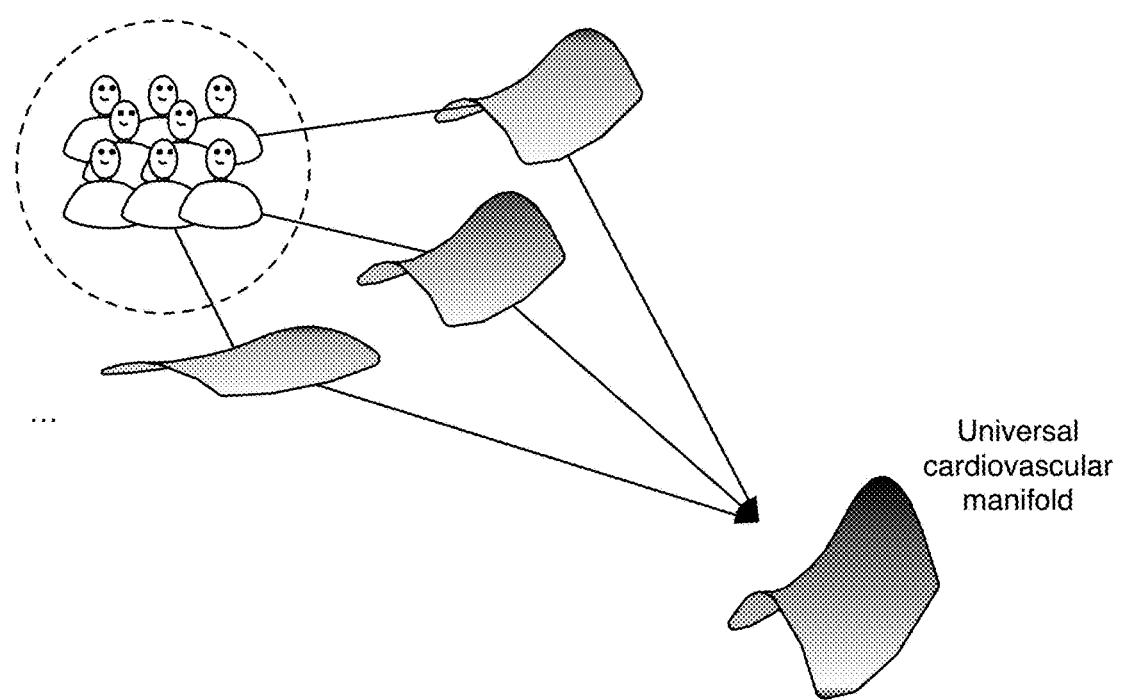
FIG. 6A is a schematic representation of an example of determining a cardiovascular manifold for a patient control group and generating a universal cardiovascular manifold.
Figure 6B:
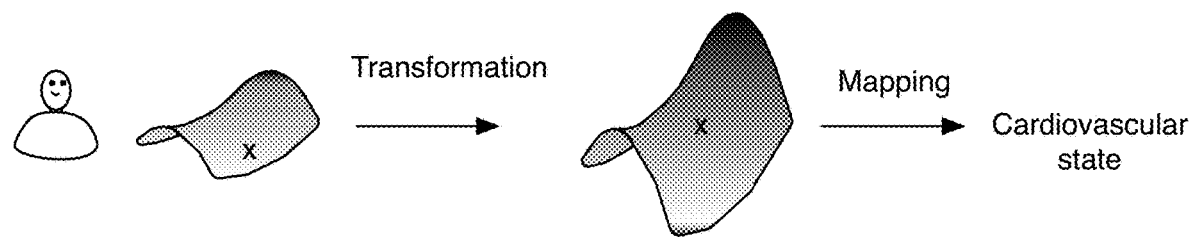
FIG. 6B is a schematic representation of an example of determining a cardiovascular state of an individual based on a transformation from the individual's cardiovascular manifold to the universal cardiovascular manifold of FIG. 6A and a mapping from a position ('x') on the universal cardiovascular manifold to a cardiovascular state.

In a second variant of S236, as shown for example in FIG. 6B, the cardiovascular parameters can be determined based on where the individual is on the individual's cardiovascular manifold, a manifold transformation from the individual's cardiovascular manifold to a universal cardiovascular manifold, and optionally a mapping transformation from the individual's position on the universal cardiovascular manifold to the cardiovascular parameter values. The cardiovascular parameter can additionally or alternatively depend on a change in where the individual is on the cardiovascular manifold, the individual's effective location on the universal cardiovascular manifold, the change in the individual's effective location on the universal cardiovascular manifold, and/or otherwise depend on the individual's relationship to the cardiovascular manifold. The universal cardiovascular manifold can be determined from the calibration dataset (as shown for example in FIG. 6A), determined from a model, generated using machine learning (e.g., a neural network), and/or be otherwise determined. The universal cardiovascular manifold can be an average of, include extrema of, be learned from (e.g., using machine learning algorithm to determine), be selected from, and/or otherwise be determined based on the calibration dataset. The universal cardiovascular manifold preferably maps values for one or more fiducials to values for cardiovascular parameters, but can be otherwise constructed. The universal cardiovascular manifold preferably encompasses at least a majority of the population's possible fiducial values and/or cardiovascular parameter values, but can encompass any other suitable swath of the population. The universal cardiovascular manifold can be specific to one or more cardiovascular parameters (e.g., the system can include different universal manifolds for blood pressure and oxygen levels), but can alternatively encompass multiple or all cardiovascular parameters of interest. The manifold transformation can include one or more affine transformation (e.g., any combination of one or more: translation, scaling, homothety, similarity transformation, reflection, rotation, and shear mapping) and/or any suitable transformation. In an illustrative example of the second variant, the individual's cardiovascular phase can be determined and aligning (e.g., using a transformation) the individual's cardiovascular phase to a universal cardiovascular phase (e.g., associated with a universal cardiovascular manifold), where a relationship between the universal cardiovascular phase and the cardiovascular parameters is known.

In a specific example, the method includes: generating the universal manifold from population calibration data, generating an individual manifold from an individual's calibration data, and determining a transformation between the individual manifold and the universal manifold. The universal manifold is preferably a finite domain and encompasses all (or a majority of) perturbations and corresponding cardiovascular parameter values (e.g., responses), but can encompass any other suitable space. The universal manifold preferably relates combinations of fiducials (with different values) with values for different cardiovascular parameters, but can relate other variables. The individual calibration data preferably includes cardiovascular measurements (e.g., PPG data, plethysmogram data) corresponding to cardiovascular parameter measurements (e.g., blood pressure), but can include other data. The population calibration data preferably includes data similar to the individual calibration data, but across multiple individuals (E.g., in one or more physiological states). The transformation can be: calculated (e.g., as an equation, as a matrix, etc.), estimated, or otherwise determined. The transformation preferably represents a transformation between the individual and universal manifolds, but can additionally or alternatively represent a mapping of the fiducial position on the universal manifold (e.g., the specific set of fiducial values, transformed into the universal domain) to the cardiovascular parameter values (e.g., in the universal domain). Alternatively, the method can apply a second transformation, transforming the universal-transformed fiducial values to the cardiovascular parameter values (e.g., in the universal domain). The transformation(s) are subsequently applied to the fiducials extracted from subsequent cardiovascular measurements from the individual to determine the individual's cardiovascular parameter values.

Figure 5:
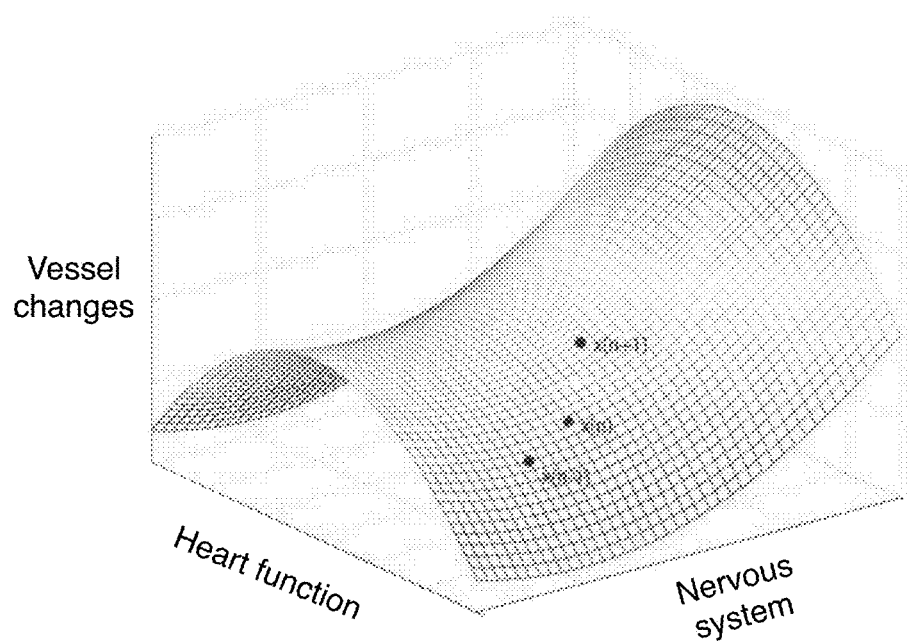
FIG. 5 is a schematic representation of an example of a cardiovascular manifold.

Embodiments of S236 can include determining a cardiovascular manifold for the individual. As shown for example, in FIG. 5, an individual's cardiovascular manifold can correspond to a surface relating the individual's heart function, nervous system, and vessel changes. However, the cardiovascular manifold can additionally or alternatively depend on the individual's endocrine system, immune system, digestive system, renal system, and/or any suitable systems of the body. The cardiovascular manifold can additionally or alternatively be a volume, a line, and/or otherwise be represented by any suitable shape. The individual's cardiovascular manifold is preferably substantially constant (e.g., slowly varies such as does not differ day-to-day, week-to-week, month-to-month, year-to-year, etc.) across the individual's lifespan. As such, an individual's cardiovascular manifold can be stored to be accessed at and used for analyzing the individual's cardiovascular parameters at a later time. However, an individual's cardiovascular manifold can be variable and/or change considerably (e.g., as a result of significant blood loss, as a side effect of medication, etc.) and/or have any other characteristic over time.

In some variants, the cardiovascular manifold can correspond to and/or be derived from the predetermined functional form (e.g., from the third variant of S232). However, the cardiovascular manifold can be otherwise related to and/or not related to the fiducials.

The cardiovascular manifold preferably corresponds to a hyperplane, but can additionally or alternatively correspond to a trigonometric manifold, a sigmoidal manifold, hypersurface, higher-order manifold, and/or be described by any suitable topological space.

Figure 9:
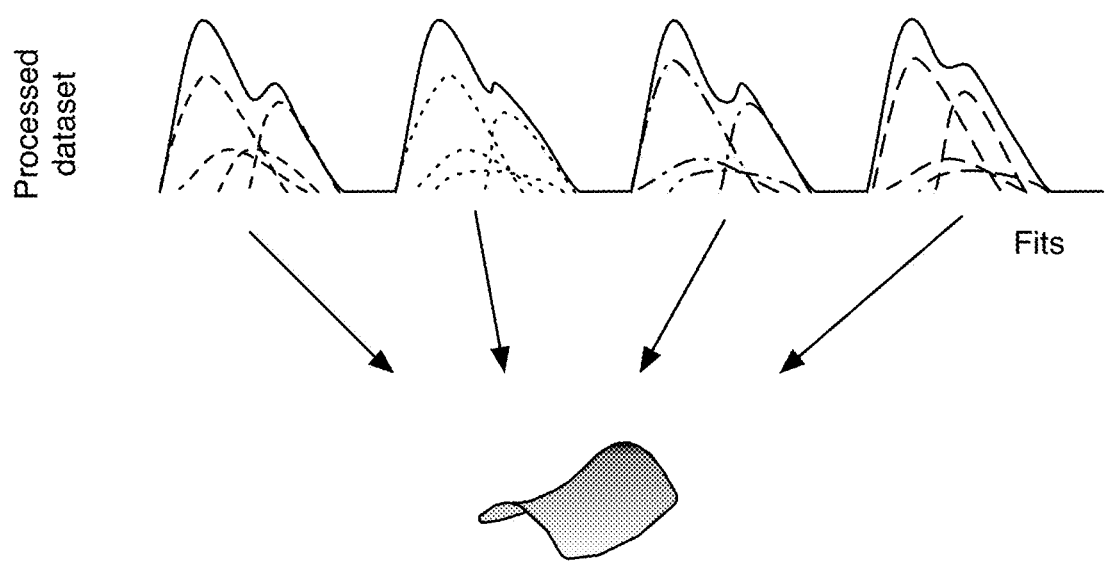
FIG. 9 is a schematic representation of an example of determining a cardiovascular manifold of a patient based on fits corresponding to segments of a PPG dataset.

As shown for example in FIG. 9, determining the cardiovascular manifold for the individual can include fitting each of a plurality of segments of a dataset (e.g., segmented dataset, processed dataset, subset of the dataset, etc.) to a plurality of gaussian functions such as, $$\hat{f}(t) = \sum_i^N p_{a_i}(\langle \varphi \rangle) e^{-\frac{(p_{b_i}(\langle \varphi \rangle)-t)^2}{p_{c_i}(\langle \varphi \rangle)}}$$

Where $\hat{f}(t)$ is the segment of the dataset, t is time, N is the total number of functions being fit, i is the index for each function of the fit; a,b, and c are fit parameters, and $p_{x_i}$ are functions of the cardiovascular phase $\langle \varphi \rangle$ where the fit parameters are constrained to values of $p_{x_i}$. The constraining functions can be the same or different for each fit parameter. The constraining functions are preferably continuously differentiable, but can be continuously differentiable over a predetermined time window and/or not be continuously differentiable. Examples of constraining functions include: constants, linear terms, polynomial functions, trigonometric functions, exponential functions, radical functions, rational functions, combinations thereof, and/or any suitable functions.

In a third variant, determining the cardiovascular parameters can include determining the cardiovascular parameters based on the supplemental data. For example, the fiducial transformation and/or manifold transformation can be modified based on the supplemental data (such as to account for a known bias or offset related to an individual's gender or race).

In a fourth variant, the cardiovascular parameters can be determined in more than one manner. For example, the cardiovascular parameters can be determined according to two or more of the above variants. In the fourth variant, the individual cardiovascular parameters can be the average cardiovascular parameter, the most probable cardiovascular parameters, selected based on voting, the most extreme cardiovascular parameter (e.g., highest, lowest, etc.), depend on previously determined cardiovascular parameters, and/or otherwise be selected.

However, the cardiovascular parameters can be determined in any suitable manner.

The method can optionally include determining a classification for the cardiovascular state. Examples of cardiovascular state classifications (CSC) include: resting, exercising, deep breathing, shallow breathing, sympathetic activation, parasympathetic activation, hypoxic, hyperoxic, and/or other classifications. The CSC is preferably determined based on the values of a set of cardiovascular parameters, but can additionally or alternatively be determined based on auxiliary data (e.g., contextual data such as time of day, ambient temperature, medications taken, etc.; physiological measurements; etc.), and/or other data. The CSC can be determined using: a classifier (e.g., RNN, CNN, autoencoder, KNN, etc.), correlations, rules, heuristics (e.g., wherein the CSC is labelled with a given class when a set of predetermined cardiovascular parameters have values within a set of respective ranges, etc.), and/or otherwise determined.

In some embodiments, S236 can include predicting an effect of one or more predetermined activities on the individual's cardiovascular parameter(s). The predicted effect can be determined based on a set of predicted fiducials if the individual were to perform the predetermined activities, a predicted position on the individual's cardiovascular manifold, a predicted effective position on the universal cardiovascular manifold, a simulated dataset (e.g., raw dataset, processed dataset, simulated dataset analogous to a dataset produced by steps S210-S228, etc.), and/or otherwise be predicted.

S239 preferably functions to store the cardiovascular parameters (and/or any suitable dataset(s)) at a client database, clinician database, user database, and/or at any suitable location/component. S239 can optionally include tracking the cardiovascular parameters over time (e.g., throughout an hour, a day, week, month, year, decade, and/or any amount of time therebetween). For example, the cardiovascular parameters for an individual can be tracked for a predetermined amount of time to monitor how stable to cardiovascular parameter is, how engagement in an activity (e.g., a predetermined activity) impacts the cardiovascular parameter(s), and/or otherwise track the cardiovascular parameters of the individual. However, S239 can be otherwise used.

S240 preferably functions to present (e.g., display) cardiovascular parameters (and/or any suitable dataset(s) or analysis thereof) to an individual, clinician, care-provider, guardian, and/or any suitable individual. S240 is preferably performed at an interface device (e.g., of a user device, of a care-provider device, of a guardian device, of a clinician device, etc.); however, any suitable component can be used to present the analysis. The cardiovascular parameters can be displayed graphically, numerically (e.g., as a percentile, as an absolute value, etc.), in a table, using an indicator (e.g., "good" or "bad"), as a change relative to previous readings, and/or be otherwise displayed. S240 can occur before, during, and/or after S230.

In variants, S240 can present one or more predetermined activities to the individual (and/or clinician, care-provider, guardian, etc.). In these variants, the predetermined activities are preferably selected to elicit a positive change in the user's cardiovascular parameter, but can additionally or alternatively present a negative change (e.g., to try to discourage the individual from partaking in the predetermined activity), and/or produce no change. The predetermined activities can be selected based on a predicted impact of the predetermined activity (e.g., as predicted in variants of S236), probabilities that the predetermined activity will have an impact, In related variants, S240 can include presenting an analysis of the individual's cardiovascular parameter(s) across time, which can show how one or more activity the individual engages in influences the individual's cardiovascular parameters. The time can be minutes, hours, days, weeks, months, years, decades, and/or any suitable time therebetween to show either long-term or short-term (e.g., immediate) impacts to the individual's cardiovascular parameters.

S250 can optionally include determining a physiological state, which can function to determine values for a set of physiological parameters. Examples of physiological parameters that can be determined include: cardiovascular parameters, body temperature, hormonal parameters (e.g., level, rate of change, etc.), immunological functions, and/or other parameters. The physiological state can be determined based on the cardiovascular parameter values, the fiducial values, auxiliary information (e.g., time of day, ambient temperature, medication schedules, etc.), and/or other information. The physiological state can be determined based on the information for: a given time window, across multiple time frames (e.g., wherein the physiological state can be determined based on parameter changes over time), and/or other temporal datasets. The physiological state can be determined using: a neural network (e.g., trained based on historical data), correlations, a lookup table, a secondary universal manifold mapping the inputs to a physiological state, or otherwise determined.

In a specific example the method 200 can include: measuring a raw PPG dataset (e.g., at a 60 Hz frame rate); generating an interpolated raw dataset by interpolating the raw PPG dataset to a standard frame rate (e.g., 240 Hz); generating a filtered dataset by filtering the interpolated raw dataset (e.g., longpass filter to remove signals≤0.5 Hz); generating a segmented raw dataset by segmenting the interpolated raw dataset (e.g., based on slow and fast moving averages, into arterial pressure waveforms corresponding to individual heartbeats, etc.); generating a denoised segmented dataset by: decomposing the segmented raw dataset (e.g., using EEMD) into a set of intrinsic modes and summing a subset of the intrinsic modes (such as the first six intrinsic modes); determining a processed dataset (e.g., a subset of the denoised segmented dataset) based on the signal-to-noise ratio of moving time windows of the denoised segmented dataset; determining fiducials from the processed dataset (e.g., fiducials for each segment of the analysis dataset); and determining the cardiovascular parameters of the individual based on the fiducials. In this specific example, determining fiducials from the analysis dataset can include fitting the analysis dataset to a spline function; calculating the first, second, and third derivatives of the fit analysis dataset; determining the roots of the first, second, and third derivatives. However, the cardiovascular parameters can be determined in any suitable manner.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. A method for determining a blood pressure of a patient, comprising:
receiving a plurality of images of a finger region of the user, wherein the images are recorded using an image recording device of a user device associated with the patient wherein the image recording device is in contact with the finger region of the user;
generating a photoplethymogram (PPG) dataset from the plurality of images;
reducing noise in the PPG dataset to generate a denoised PPG dataset by:
filtering the PPG dataset using a longpass filter configured to remove signals from the PPG dataset below 0.5 Hertz;
decomposing the PPG dataset into a set of modes using enhanced empirical mode decomposition;
extracting intrinsic modes from the set of modes; and
aggregating the intrinsic modes to generate the denoised PPG dataset;
segmenting the denoised PPG dataset into a segmented PPG dataset using moving average segmentation;
determining a processed PPG dataset by averaging a predetermined number of segments of the segmented PPG dataset;
extracting a set of fiducials from for each segment of the processed PPG dataset comprising:
calculating the first, the second, and the third derivative of the segment;
determining time points corresponding to zeros of the first, second, and third derivative;
determining values of the segment at the time points;
determining values of the first, second, and third derivatives of the segment at the time points;
determining a position on a patient cardiovascular manifold, relating a heart function, nervous system, and vascular system of the patient, based on the set of fiducials;
transforming the position on the patient cardiovascular manifold to a position on a universal cardiovascular manifold; and
determining the blood pressure of the patient based on a mapping from the position on the universal cardiovascular manifold to a blood pressure value;
wherein the set of fiducials comprises:
the values of the segmented PG dataset for time points corresponding to the first four zeros of the first and second derivatives;
the values of the first derivative of the processed PG dataset for the time points corresponding to the first four zeros of the first and second derivatives; and
the values of the second derivative of the processed PG dataset for the time points corresponding to the first four zeros of the first and second derivatives.

2. The method of claim 1, wherein the predetermined number of segments comprises at least 10 segments of the PPG dataset.

3. The method of claim 1, wherein at least one of the universal cardiovascular manifold or the transformation are determined by:
for each patient of a group of calibration patients:
measuring a blood pressure using at least one of a sphygmomanometer, a digital blood pressure monitor, radial artery tonometry, arterial catheter, or electrocardiogram;
contemporaneously with measuring the blood pressure, determining a set of fiducials corresponding to the calibration patient; and
determining a relationship between the measured blood pressure and the set of fiducials; and
combining the relationship for each patient to determine at least one of the universal cardiovascular manifold or the transformation.

4. The method of claim 1, wherein extracting the set of fiducials from the processed PPG dataset comprises fitting the processed PPG dataset to a fitting function, wherein the set of fiducials comprises one or more fit parameters of the fitting function.

5. The method of claim 4, wherein the fitting function comprises a plurality of gaussians.

6. The method of claim 4, wherein the fit parameters are constrained to values of a hyperplane.

7. A method for determining a cardiovascular state of a patient, comprising:
receiving a plethymogram (PG) dataset measured at a finger region of the patient;
removing noise from the PG dataset by aggregating a set of intrinsic modes corresponding to the PG dataset;
segmenting the denoised PG dataset into a segmented PG dataset, wherein each segment corresponds to a cardiac cycle of the patient;
extracting a set of fiducials for each segment of the segmented PG dataset, wherein the set of fiducials is determined based on values of at least one of:
the segmented PG dataset,
a first derivative of the segmented PG dataset,
a second derivative of the segmented PG dataset, or
a third derivative of the segmented PG dataset; and
determining the cardiovascular state of the patient by applying a transformation to the set of fiducials;
wherein extracting a set of fiducials for each segment of the segmented PG dataset comprises:
calculating the first, the second, and the third derivative of the segment;
determining time points corresponding to zeros of the first, second, and third derivative;
determining values of the segment at the time points;
determining values of the first, second, and third derivatives of the segment at the time points; and
wherein the set of fiducials comprises:
the values of the segmented PG dataset for time points corresponding to the first four zeros of the first and second derivatives;
the values of the first derivative of the processed PG dataset for the time points corresponding to the first four zeros of the first and second derivatives; and
the values of the second derivative of the processed PG dataset for the time points corresponding to the first four zeros of the first and second derivatives.

8. The method of claim 7, further comprising: interpolating between data points in the PG dataset to fill gaps in the PG dataset.

9. The method of claim 7, wherein the cardiovascular state of the patient comprises one or more of: a blood pressure, a cardiac event, cardiovascular drift, and a drug reaction of the patient.

10. The method of claim 7, wherein reducing the noise in the PG dataset further comprises filtering the PG dataset using a long pass filter.

11. The method of claim 7, wherein the set of intrinsic modes are determined using enhanced empirical mode decomposition.

12. The method of claim 11, wherein removing noise from the PG dataset comprises aggregating the first six modes of the set of intrinsic modes.

13. The method of claim 7, wherein segmenting the denoised PG dataset comprises segmenting the denoised PG dataset by detecting a moving-average crossover.

14. The method of claim 7, further comprising determining an average PG dataset by averaging a predetermined number of segments of the segmented data, wherein the set of fiducials is determined based on the averaged PG dataset.

15. The method of claim 7, further comprising:
  determining a patient cardiovascular manifold, relating a heart function, nervous system, and vascular system of the patient, based on the set of fiducials; and
  determining a manifold transformation that converts the patient cardiovascular manifold to a universal cardiovascular manifold;
wherein the transformation comprises the manifold transformation.

16. The method of claim 7, wherein the transformation is determined based on a calibration dataset generated based on cardiovascular state measurements derived from a group of calibration patients.

17. The method of claim 7, wherein the transformation is a linear transformation.

* * * * *